(12) United States Patent
Hirahara et al.

(10) Patent No.: US 9,114,084 B2
(45) Date of Patent: Aug. 25, 2015

(54) CLEANING AGENT COMPOSITION

(75) Inventors: Mayuko Hirahara, Bunkyo-ku (JP); Izumi Katsuta, Bunkyo-ku (JP)

(73) Assignee: KAO CORPORATION, Tokyo (JP)

( * ) Notice: Subject to any disclaimer, the term of this patent is extended or adjusted under 35 U.S.C. 154(b) by 0 days.

(21) Appl. No.: 14/114,544

(22) PCT Filed: May 1, 2012

(86) PCT No.: PCT/JP2012/061554
§ 371 (c)(1),
(2), (4) Date: Oct. 29, 2013

(87) PCT Pub. No.: WO2012/150710
PCT Pub. Date: Nov. 8, 2012

(65) Prior Publication Data
US 2014/0076343 A1 Mar. 20, 2014

(30) Foreign Application Priority Data
May 2, 2011 (JP) .................................. 2011-103054

(51) Int. Cl.
*A61Q 19/10* (2006.01)
*A61K 8/18* (2006.01)
*A61K 8/46* (2006.01)
*A61K 8/73* (2006.01)
*C08B 11/193* (2006.01)
*C08L 1/26* (2006.01)
*C08L 1/28* (2006.01)
*A61K 8/81* (2006.01)

(52) U.S. Cl.
CPC ...... *A61K 8/18* (2013.01); *A61K 8/46* (2013.01); *A61K 8/463* (2013.01); *A61K 8/731* (2013.01); *A61K 8/817* (2013.01); *A61Q 19/10* (2013.01); *C08B 11/193* (2013.01); *C08L 1/26* (2013.01); *C08L 1/284* (2013.01)

(58) Field of Classification Search
None
See application file for complete search history.

(56) References Cited

U.S. PATENT DOCUMENTS

| | | | |
|---|---|---|---|
| 3,816,616 A | 6/1974 | Anguillo et al. | |
| 6,312,678 B1 | 11/2001 | Elliott et al. | |
| 6,444,629 B1 | 9/2002 | Elliott et al. | |
| 7,960,327 B2 * | 6/2011 | Uchiyama et al. | 510/130 |
| 2008/0261845 A1 | 10/2008 | Yamamoto et al. | |
| 2008/0287393 A1 * | 11/2008 | Sayo et al. | 514/62 |
| 2009/0253603 A1 | 10/2009 | Uchiyama et al. | |
| 2012/0214985 A1 | 8/2012 | Takai et al. | |
| 2012/0230934 A1 | 9/2012 | Doi et al. | |

FOREIGN PATENT DOCUMENTS

| | | |
|---|---|---|
| CN | 101484568 A | 7/2009 |
| CN | 102596166 A | 7/2012 |
| EP | 2 500 012 A1 | 9/2012 |
| JP | 59 42681 | 10/1984 |
| JP | 2001 513538 | 9/2001 |
| JP | 2001 513539 | 9/2001 |
| JP | 2005 306843 | 11/2005 |
| JP | 2008-179583 A | 8/2008 |
| JP | 2008-285479 A | 11/2008 |
| JP | 2009-102267 A | 5/2009 |
| JP | 2009-263289 A | 11/2009 |
| JP | 2009-263290 A | 11/2009 |
| JP | 2009 263291 | 11/2009 |
| JP | 2010-70508 A | 4/2010 |
| JP | 2011 37727 | 2/2011 |
| WO | WO 2008004342 * | 1/2008 |
| WO | 2011 059063 | 5/2011 |
| WO | 2012 091072 | 7/2012 |

OTHER PUBLICATIONS

Extended European Search Report issued Nov. 6, 2014 in Patent Application No. 12779396.6.
U.S. Appl. No. 14/115,193, filed Nov. 1, 2013, Hirahara, et al.
(Continued)

*Primary Examiner* — Jyothsna Venkat
(74) *Attorney, Agent, or Firm* — Oblon, McClelland, Maier & Neustadt, L.L.P.

(57) ABSTRACT

A cleansing composition comprising the following components (A), (B), (C) and (D):
 (A) from 1 to 20% by weight of a polyoxyethylene alkyl ether sulfate,
 (B) from 0.02 to 5% by weight of a cation group-containing polymer (B) having a cationic charge density of from 4.5 to 7 meq/g,
 (C) from 0.02 to 10% by weight of cationized hydroxypropyl cellulose (C) represented by the following formula (1)
wherein $R^1$, $R^2$ and $R^3$ each independently represent a substituent group having a cationized ethyleneoxy group and a propyleneoxy group, n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5, and
 (D) water.

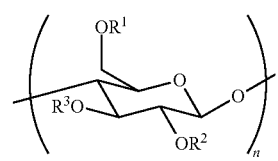

(1)

7 Claims, No Drawings

(56) References Cited

OTHER PUBLICATIONS

U.S. Appl. No. 14/115,521, filed Nov. 4, 2013, Hirahara, et al.
International Preliminary Report on Patentability and Written Opinion issued Nov. 14, 2013 in PCT/JP2012/061554.
International Preliminary Report on Patentability and Written Opinion issued Nov. 14, 2013 in PCT/JP2012/061553.
International Search Report Issued Aug. 14, 2012 in PCT/JP12/061554 Filed May 1, 2012.
Fragrance Journal, vol. 36, No. 12, (Dec. 15, 2008), pp. 38-43 (with unedited computer generated English translation).
New cosmetics handbook, Nikko Chemicals Co., Ltd., (Oct. 30, 2006), pp. 635-636 (with unedited computer generated English translation).
New cosmetics handbook Sunlight Chemical Co., Ltd. Four Others, (Oct. 30, 2006), pp. 237-238 (with unedited computer generated English translation).
Fragrance Journal, vol. 26, No. 1, (Jan. 15, 1998), pp. 107-111 (with unedited computer generated English translation).

* cited by examiner

CLEANING AGENT COMPOSITION

FIELD OF THE INVENTION

The present invention relates to a cleansing composition.

BACKGROUND OF THE INVENTION

Among various performances required for skin cleansing compositions for cleansing the face and body, quick disappearance of slimy feel and a feel with frictional resistance (stop feeling) is important as a feel to the touch during rinsing after cleansing. Allowing the slimy feel to more quickly disappear in the course of rinsing and allowing the skin to have stronger sense of stop feeling are more preferred, because a refreshed clean feeling can be obtained.

Skin cleansing compositions containing a polyoxyethylene alkyl ether sulfate, which is a surfactant commonly employed in the present field of art, as a main ingredient have conventionally been accompanied by a problem that a slimy feel during rinsing remains, although the compositions have good lathering ability.

Patent Documents 1 and 2 disclose that an improved rinse feeling is available upon rinsing when a water-insoluble oil such as polyisobutene or silicone oil is added to a personal cleansing composition containing, as a main component, a water-soluble surfactant such as a polyoxyethylene alkyl ether sulfate.

However, the addition of an oil component to a skin cleansing composition as mentioned above has such a problem that, especially when used to cleanse the body, a stop feeling is not sufficient upon rinsing and a residual feeling of the oil component on the skin and its oily feeling remain strong after being rinsed off, and therefore, there is a problem that the skin remains sticky and no refreshed feeling to the touch is available.

In Patent Document 3, a skin cleansing composition containing a specific surfactant and a cationic polymer is disclosed. In a hair cleansing agent, the cationic polymer is used as a conditioning agent for lowering frictional feel, and thus finger combing is improved during rinsing. Also in a skin cleansing agent, it is used as a conditioning agent to impart moist feeling to skin.

CITATION LIST

Patent Document

Patent Document 1: JP-A-2001-513539
Patent Document 2: JP-A-2001-513538
Patent Document 3: JP-A-2005-306843

SUMMARY OF THE INVENTION

The invention is to provide a cleansing composition comprising the following components (A), (B), (C), and (D):

(A) from 1 to 20% by weight of a polyoxyethylene alkyl ether sulfate;

(B) from 0.02 to 5% by weight of a cation group-containing polymer having a cationic charge density of from 4.5 to 7 meq/g;

(C) from 0.02 to 10% by weight of cationized hydroxypropyl cellulose represented by the following formula (1);

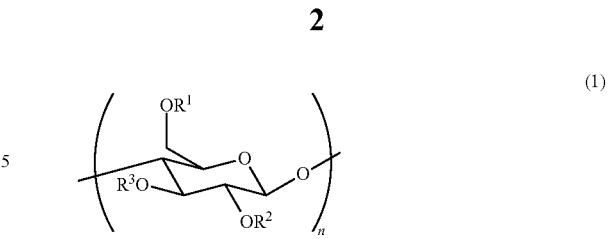

wherein, $R^1$, $R^2$ and $R^3$ each independently represent a substituent group having a cationized ethyleneoxy group and a propyleneoxy group represented by the following formula (2) or (3), n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5.

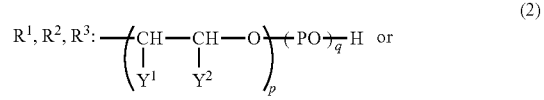

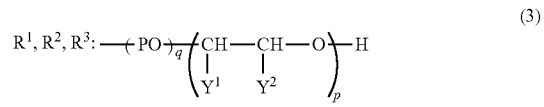

wherein, one of $Y^1$ and $Y^2$ represents a hydrogen atom and the other is a cationic group represented by the following formula (4), PO represents a propyleneoxy group, p represents the number of the cationized ethyleneoxy group ($-CH(Y^1)-CH(Y^2)-O-$) contained in the formula (2) or (3), q represents the number of the propyleneoxy group ($-PO-$) contained in the formula (2) or (3), each representing 0 or a positive number, in which, when none of p and q is 0, the cationized ethyleneoxy group and propyleneoxy group may be added in any order, and when at least one selected from p and q is 2 or higher, it may be any one of a block bond and a random bond.

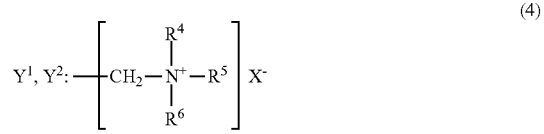

wherein, $R^4$, $R^5$ and $R^6$ each independently represent a linear or branched alkyl group having from 1 to 3 carbon atoms, and $X^-$ represents an anionic group, and (D) water.

DESCRIPTION OF EMBODIMENTS

In the intended use of skin cleansing, conventional cleansing compositions are not completely satisfactory in that there are causes for slimy feel which persists for a long period of time and stop feeling is hardly expressed during rinsing.

The present invention relates to a cleansing composition which exhibits a high lathering property and excellent cleansing feel during use, has a strong stop feeling property due to quick disappearance of slimy feel during rinsing, and provides an excellent feel to the touch of the skin after drying.

The inventors of the present invention found that, by combining polyoxyethlyene alkyl ether sulfate with two specific kinds of a cationic group-containing polymer, a cleansing composition which exhibits a high lathering property and excellent cleansing feel during use, has strong stop feeling property due to quick disappearance of slimy feel during rinsing, and provides an excellent feel to the touch of the skin after drying can be provided.

The cleansing composition of the present invention has excellent cleansing feel due to large foam volume during cleansing, stop feeling with high frictional resistance due to easy wash-off based on quick disappearance of slimy feel during rinsing, and provides smooth feeling accompanied with moistness and softness after cleansing. In addition, the skin immediately after towel dried can be given with a feel to the touch like being protected with a film with no stickiness.

As for the polyoxyethlyene alkyl ether sulfate used as the component (A) in the present invention, those represented by the following formula are preferable.

R—O(CH$_2$CH$_2$O)$_n$—SO$_3$X wherein, R represents an alkyl group or an alkenyl group having from 10 to 18 carbon atoms, n represents a number of from 0.5 to 5 on average, and X represents a hydrogen atom, an alkali metal, an alkali earth metal, ammonium or organic ammonium.

In the formula, an alkyl group having from 12 to 14 carbon atoms may be preferred as R. The average addition mole number of ethylene oxide is preferably in the range from 0.5 to 5, more preferably from 0.9 to 4, and even more preferably from 1 to 3.

Further, as X, an alkali metal such as sodium or potassium; an alkali earth metal such as calcium or magnesium; ammonium; an ammonium derived from an alkanolamine such as monoethanolamine, diethanolamine or triethanolamine; a cation derived from a basic amino acid such as arginine or lysine, and the like may be mentioned. Among them, from the viewpoint of less coloration of the composition, an alkali metal salt and ammonium salt are preferable. An alkali metal salt is more preferable.

One or two or more types of the component (A) may be used. From the viewpoint of having washability, lathering speed, and less rough dry skin after cleansing, it may be contained, as a salt in the total composition, at 1% by weight or more, and preferably 3% by weight or more, but 20% by weight or less, and preferably 12% by weight or less. Taken together the above aspects, as a salt in the total composition, it is contained at from 1 to 20% by weight, and preferably from 3 to 12% by weight.

The component (B) used in the present invention is a cationic group-containing polymer which has cationic charge density of from 4.5 to 7 meq/g.

It is noted that the term "cationic charge density" as used herein means the number (meq/g) of equivalents of cationic charges in monomer units which constitute a polymer.

Examples of the cationic group-containing polymer having a cationic charge density of 4.5 meq/g or more as the component (B) include homopolymer of dimethyl diallylammonium chloride; copolymers of dimethyl diallylammonium chloride with other monomers such as (meth)acrylic acid, (meth)acrylate esters, (meth)acrylamides; and polymethacryloyloxyethyl trimethylammonium chloride, and the like.

More specific examples include homopolymer of dimethyl diallylammonium chloride ("MERQUAT 100"; manufactured by Ondeo Nalco Co.; charge density: 6.2 meq/g), a copolymer of dimethyl diallylammonium chloride and acrylic acid ("MERQUAT 295"; manufactured by Ondeo Nalco Co.; charge density: 6.0 meq/g); a copolymer of dimethyl diallylammonium chloride and acrylic acid ("MER-QUAT 280"; manufactured by Ondeo Nalco Co.; charge density: 5.0 meq/g); polymethacryloyloxyethyl trimethylammonium chloride (manufactured by Kao Corporation; charge density: 4.8 meq/g), and the like.

The cationic charge density of the cationic group-containing polymer is 4.5 meq/g or more, preferably from 4.5 to 7 meq/g, more preferably from 5 to 7 meq/g, and even more preferably from 5.5 to 6.5 meq/g. With one having a high cationic charge density in this range, a good stop feeling can be obtained upon rinsing the cleansing composition. In particular, the homopolymer of dimethyl diallylammonium chloride ("MERQUAT 100"; manufactured by Ondeo Nalco Co.; charge density: 6.2 meq/g) and the copolymers of dimethyl diallylammonium chloride and acrylic acid in which the weight ratio of dimethyl diallylammonium chloride to acrylic acid is 97:3 ("MERQUAT 295"; manufactured by Ondeo Nalco Co.; charge density: 6.0 meq/g) are more preferred from the viewpoints of stop feeling upon rinsing.

As for the polymer of the component (B), the homopolymer of dimethyldiallyl ammonium chloride and the copolymers of dimethyldiallyl ammonium chloride and acrylic acid are preferred from the viewpoint of the corrosion resistance of production facilities.

One or two or more types of the component (B) may be used. From the viewpoint of having excellent foam quality during cleansing, it may be contained at 0.02% by weight or more, preferably 0.1% by weight or more, and more preferably 0.2% by weight or more, but 5% by weight or less, preferably 1.5% by weight or less, and more preferably 0.8% by weight or less. Taken together the above aspects, as a salt in the total composition, it is contained at from 0.02 to 5% by weight, preferably from 0.1 to 1.5% by weight, and more preferably from 0.2 to 0.8% by weight.

The component (C) used in the present invention is cationized hydroxypropyl cellulose represented by the above formula (1), in which main chain derived from anhydroglucose is contained, the substitution degree of the cationized ethyleneoxy group is from 0.01 to 3, and the substitution degree of the propyleneoxy group is from 0.01 to 5 (hereinafter, also referred to as "C-HPC").

(Main Chain Derived from Anhydroglucose Represented by the Formula (1))

The main chain derived from anhydroglucose, which is represented by the formula (1), has a main chain derived from anhydroglucose, as represented in the above formula (1).

In the formula (1), $R^1$, $R^2$ and $R^3$ each independently represent a substituent group represented by the formula (2) or (3), in which $R^1$, $R^2$ and $R^3$ may be the same or different from each other. In addition, each of $R^1$ in the number of n, $R^2$ in the number of n, and $R^3$ in the number of n may be the same or different from each other.

From the viewpoint of having stop feeling during rinsing after washing with the cleansing composition of the present invention and good smoothness with moist feeling of skin after drying, the average polymerization degree n in the formula (1) is 20 or higher, preferably 100 or higher, and more preferably 400 or higher. Further, the upper limit is 5000 or lower, preferably 2000 or lower, and more preferably 1300 or lower. Taken together the above aspects, the average polymerization degree n in the formula (1) is from 20 to 5000, preferably 100 to 2000, and more preferably from 400 to 1300.

Meanwhile, as described herein, the average polymerization degree indicates viscosity average polymerization degree that is measured by copper-ammonia method, and it is specifically calculated by the method described in Examples.

(Substituent Group Represented by the Formula (2) or (3))

In the formula (1), the substitution group represented by the formula (2) or (3) as $R^1$, $R^2$ or $R^3$ has a cationized ethyleneoxy group and a propyleneoxy group as represented in the above formula (2) or (3).

In the formula (2) or (3), one of $Y^1$ and $Y^2$ is a hydrogen atom and the other is a cationic group represented by the formula (4), and PO represents a propyleneoxy group.

p represents the number of the cationized ethyleneoxy group (—CH($Y^1$)—CH($Y^2$)—O—) in the formula (2) or (3), and it is 0 or a positive number. From the viewpoint of ease of production, p is preferably 0 or 1.

q represents the number of the propyleneoxy group (—PO—) in the formula (2) or (3), and it is 0 or a positive number. From the viewpoint of ease of production, q is preferably a number of from 0 to 4, more preferably a number of from 0 to 2, and even more preferably 0 or 1.

When various substituent groups represented by the formula (2) are present in a C-HPC molecule, each of p and q may be different among the substituent groups.

From the viewpoint of ease of production, the sum of p and q is preferably a number of from 1 to 5, more preferably a number of from 1 to 4, more preferably a number of from 1 to 3, and even more preferably 1 or 2.

When none of p and q is 0, the cationized ethyleneoxy group and propyleneoxy group may be added in any order. However, from the viewpoint of production efficiency, it is preferably an order described in the formula (3).

In addition, when none of p and q is 0 and at least one selected from p and q is 2 or higher, it is sufficient to have any one of a block bond and a random bond. However, from the viewpoint of ease of production, it is preferably a block bond.

In at least one of $R^1$ in the number of n, $R^2$ in the number of n, and $R^3$ in the number of n, p in the formula (2) or (3) is not 0, and in at least one of them, q in the formula (2) or (3) is not 0.

(Cationic Group Represented by the Formula (4))

In the formula (2) or (3), the cationic group represented by the formula (4) as $Y^1$ and $Y^2$ has a structure represented by the above formula (4).

$R^4$, $R^5$ and $R^6$ in the formula (4) each independently represent a linear or branched alkyl group having from 1 to 3 carbon atoms, and specific examples thereof include a methyl group, an ethyl group, a n-propyl group and an isopropyl group. Among them, from the viewpoint of water solubility of C-HPC, a methyl group and an ethyl group are preferable, and a methyl group is more preferable.

In the formula (4), $X^-$ represents an anionic group as a counter ion of the ammonium group. $X^-$ is not limited, if it is an anionic group. Specific examples thereof include an alkyl sulfate ion, a sulfate ion, a phosphate ion, an alkyl carbonate ion, a halide ion, and the like. Among them, from the viewpoint of ease of production, a halide ion is preferable. Examples of the halide ion include a fluoride ion, a chloride ion, a bromide ion, and an iodide ion. From the viewpoint of water solubility and chemical stability of C-HPC, a chloride ion and a bromide ion are preferable, and a chloride ion is more preferable.

In C-HPC represented by the formula (1), from the viewpoint of enhancing lathering ability during cleansing, having strong feel with frictional resistance (that is, stop feeling) by quickly removing slimy feel during rinsing after cleansing, and obtaining a good feel accompanying moistness after the skin is dried, the substitution degree of the cationized ethyleneoxy group is preferably from 0.01 to 3, more preferably from 0.1 to 2.4, and even more preferably from 0.18 to 1.

According to the present invention, the substitution degree of the cationized ethyleneoxy group means the average mole number of the cationized ethyleneoxy group that is present in C-HPC molecule per mole of anhydroglucose unit constituting the cellulose main chain. The substitution degree of the cationized ethyleneoxy group is measured according to the method described in the following Examples.

Further, from the viewpoint of degree of foamability during cleansing, foam dissipation during rinsing, and having foam removing property, the substitution degree of the propyleneoxy group is from 0.01 to 5, preferably from 0.2 to 3, and more preferably from 1.1 to 2.9.

According to the invention, the substitution degree of the propyleneoxy group means the average mole number of the propyleneoxy group that is present in C-HPC molecule per mole of anhydroglucose unit constituting the cellulose main chain. The substitution degree of the propyleneoxy group is measured according to the method described in the following Examples.

C-HPC of the component (C) may be obtained by the following production methods (1) to (3), for example.

(1) Cellulose, water in a large amount, and alkali metal hydroxide in an excess amount are mixed in slurry form, followed by reaction between a cationizing agent and propylene oxide.

(2) By using dimethyl acetamide containing lithium chloride as a solvent and dissolving cellulose by adding amines or an alcoholate catalyst, a cationizing agent is reacted with propylene oxide.

(3) Without using water in excess amount or solvent such as the above (1) and (2), cellulose in a powder form, a pellet form, or a chip form, a cationizing agent, and propylene oxide are reacted with one another in the presence of a base.

According to the above production methods (1) to (3), the reaction with a cationizing agent and the reaction with propylene oxide may be carried out in any order or may be carried out simultaneously.

Among the above production methods, from the viewpoint of ease of production, the production method (3) is preferable.

One or two or more types of C-HPC may be used as the component (C). From the viewpoint of foam quality during cleansing, reduction of a slimy feel during rinsing after cleansing, and having stop feeling at certain level, it is contained at 0.02% by weight or more, preferably 0.1% by weight or more, and more preferably 0.3% by weight or more in the total composition. In addition, it is 10% by weight or less, preferably 1.5% by weight or less, and more preferably 0.8% by weight or less in the total composition. Taken together the above aspects, it is contained in an amount of from 0.02 to 10% by weight, preferably from 0.1 to 1.5% by weight, and more preferably from 0.3 to 0.8% by weight in the total composition.

According to the present invention, by combining the component (A), the component (B), and the component (C), foamability and foam volume are improved during cleansing so that favorable cleansing feel can be obtained. In addition, as there is less slimy feel during rinsing but strong stop feeling after rinsing, refreshing cleansing feel can be obtained.

In the present invention, the weight ratio between the components (B) and (C) is preferably, from the viewpoint of having a feeling like being protected by a smooth film with no stickiness after drying, 0.1 or higher in terms of (C)/(B). More preferably, it is 0.4 or higher, and more preferably 0.6 or higher, but preferably 10 or less, more preferably 4 or less, and even more preferably 2 or less. Taken together the above aspects, (C)/(B) is preferably from 0.1 to 10, more preferably from 0.4 to 4, and even more preferably from 0.6 to 2.

Water as the component (D) constitutes balance of each component, and it is preferably contained in an amount of from 40 to 94% by weight in the total composition.

The cleansing composition according to the present invention may further comprise (E) an inorganic salt or an organic acid salt having 6 or less carbon atoms.

Examples of the inorganic salt include salts between alkali metals or alkali earth metals and halogens, sulfuric acid, sulfurous acid, phosphoric acid and the like. Specific examples thereof include sodium chloride, potassium chloride, sodium bromide, magnesium chloride, sodium sulfate, potassium sulfate, sodium dihydrogen phosphate, disodium hydrogen phosphate and the like. Examples of the organic acid salt include salts between acetic acid and hydroxy acids or polyacids, such as lactic acid, malic acid, citric acid and succinic acid, and alkali metals or the like.

Among them, preferred are sodium chloride, sodium malate, sodium lactate, sodium citrate, and sodium succinate.

As the component (E), one or two or more types may be used within the range not interfering the foamability or foam quality as effects of the present invention. When used, it is preferably contained at 0.1% by weight or more and more preferably 0.5% by weight or more in the total composition. In addition, it is preferably 6% by weight or less and more preferably 3% by weight or less. Taken together the above aspects, it is preferably contained in an amount of from 0.1 to 6% by weight and more preferably from 0.5 to 3% by weight in the total composition. When it is within the above range, the dissolution of the complex formed by the components (A), (B) and (C) is facilitated so that the complex in dissolution state can be contained in a large amount. Further, precipitation amount of the complex can be increased during rinsing, and therefore desirable. As a result, the stop feeling property is improved, and thus a strong stop feeling property can be obtained.

According to the invention, the weight ratio among the components (A), (B), (C), and (E) is, in terms of (E)/((A)+(B)+(C)), preferably from 0.04 to 0.3, and more preferably from 0.08 to 0.27. In such case, the dissolution of the complex formed by the three components (A), (B) and (C) is facilitated. Further, when ((B)+(C))/(A) is from 0.04 to 0.3, and also from 0.05 to 0.19, the dissolution of the complex becomes easier, and therefore desirable.

The cleansing composition of the present invention may also comprise (F) a non-ionic polymer.

Examples of the non-ionic polymer include hydroxyethyl cellulose, hydroxypropylmethyl cellulose, hydroxypropyl guar gum, polyvinyl pyrrolidone, and polyethylene glycol, and the like. Among them, polyethylene glycol is more preferable. Weight average molecular weight of them is preferably from 40,000 to 3,000,000, and more preferably from 300,000 to 2,750,000, or from 2,000,000 to 2,500,000.

Examples of the non-ionic polymer which may be used include ALKOX series (Meisel Chemical Works, Ltd., polyethylene glycol): ALKOX E30 (weight average molecular weight of from 300,000 to 500,000), ALKOX E-45 (weight average molecular weight of from 600,000 to 800,000), ALKOX E-60 (weight average molecular weight of from 1,000,000 to 1,200,000), ALKOX E-75 (weight average molecular weight of from 2,000,000 to 2,500,000), ALKOX E-100 (weight average molecular weight of from 2,500,000 to 3,000,000); METOLOSE series (Shin-Etsu Chemical Co., Ltd., hydroxypropylmethyl cellulose): METOLOSE 60SH-10000 (weight average molecular weight of 380,000); LUVISKOL series (BASF Japan, polyvinyl pyrrolidone): LUVISKOL K30 (weight average molecular weight of from 40,000 to 60,000), LUVISKOL K90 (weight average molecular weight of 1,200,000); JAGUAR HP series (hydroxypropyl guar gum manufactured by Rhodia), JAGUAR HP8, HP105, and HP-120 (all with weight average molecular weight of 2,200,000), and the like.

By combining the non-ionic polymer as the component (F) with the component (A), the component (B), and the component (C), foam quality can be improved to have a fine texture during cleansing. Further, moistness can be given to a dry skin after cleansing. When the component (F) is contained, from such point of view, it is preferably contained at 0.01% by weight or more and more preferably 0.02% by weight or more, but preferably 0.8% by weight or less and more preferably 0.4% by weight or less in the total composition. Taken together the above aspects, it is preferably contained at from 0.01 to 0.8% by weight, and more preferably from 0.02 to 0.4% by weight.

The cleansing composition of the present invention may also comprise (G) at least one selected from alkyl polyglycoside-based non-ionic surfactant and polyoxyethylene alkyl ether-based non-ionic surfactant, and thus high foam volume can be generated during cleansing.

Alkyl polyglycosides are a non-ionic surfactant derived from sugars and higher alcohols, and examples include those represented by the following formula.

$$R-O(CH_2CH_2O)_m-Z_x$$

wherein R represents an alkyl group having from 9 to 20 carbon atoms, m represents, on average, a number of 0 or higher but 10 or lower, Z represents a sugar residue having 5 or 6 carbon atoms, and x represents, on average, a number of from 1 to 5.

In the formula, R is preferably an alkyl group having from 9 to 16 carbon atoms, and it may be a mixture of them. Z is preferably pentose or hexose, and among them, glucose is more preferable. m is, on average, preferably a number of from 0 to 5, and x is, on average, preferably a number of from 1 to 3.

As a polyoxyethylene alkyl ether-based non-ionic surfactant, those having an alkyl group with from 12 to 22 carbon atoms, and those having an addition mole number of polyoxyethylene group of from 10 to 30 are preferable. Specific examples thereof include polyoxyethylene lauryl ether, polyoxyethylene myristyl ether, polyoxyethylene palmityl ether, polyoxyethylene isostearyl ether, polyoxyethylene stearyl ether, polyoxyethylene oleyl ether, polyoxyethylene hexyldecyl ether, polyoxyethylene octyldodecyl ether, polyoxyethylene behenyl ether, and the like.

Further, polyoxyethylene alkyl ether-based non-ionic surfactants having HLB of from 10 to 20, and also having HLB of from 13 to 16 are preferable because a cleansing composition having more excellent transparency can be obtained.

Meanwhile, HLB is an index indicating a balance between hydrophilicity and lipophilicity (that is, Hydropile Balance), and in the invention, the values calculated according to the equation by Oda and Teramura et al are used.

$$HLB = \frac{\sum \text{Inorganic value}}{\sum \text{Organic value}} \times 10$$

Examples of the polyoxyethylene alkyl ether-based non-ionic surfactant include polyoxyethylene (21) lauryl ether (EMULGEN 121-G (HLB 14), manufactured by Kao Corporation), polyoxyethylene (20) 2-hexyldecyl ether (EMULGEN 1620G (HLB 14), manufactured by Kao Corporation), polyoxyethylene (20) octyl dodecyl ether (EMULGEN 2020G (HLB 13), manufactured by Kao Corporation), polyoxyethylene (16) lauryl ether (EMULGEN 116 (HLB 15.8), manufactured by Kao Corporation), and the like.

As for the component (G), from the viewpoint of having an excellent skin feel of towel-dried skin after cleansing, alkyl polyglycoside is preferable.

One or more types of the component (G) may be used. When it is contained, from the viewpoint of having foam volume of the cleansing composition and a feel to the touch during rinsing, it is preferably contained in an amount of 0.05% by weight or more, more preferably 0.2% by weight or more, and even more preferably 0.5% by weight or more in the total composition. Further, it is preferably contained in an amount of 10% by weight or less, more preferably 6% by weight or less, and even more preferably 4% by weight or less in the total composition. Taken together the above aspects, it is preferably contained in an amount of from 0.05 to 10% by weight, more preferably from 0.2 to 6% by weight, and even more preferably from 0.5 to 4% by weight in the total composition.

The cleansing composition of the present invention may also comprise (H) an amphoteric surfactant.

Examples of the amphoteric surfactant include carbobetaine, sulfobetaine, imidazolium betaine, amide betaine and the like, and by using it, lathering ability can be further improved without suppressing rinsing property. Specific examples thereof include fatty acid amide propylbetaine, alkyl hydroxy sulfobetaine, and the like.

One or more types of the component (H) may be used. When it is contained, it is preferably contained in an amount of from 0.1 to 10% by weight, and also from 0.5 to 6% by weight in the total composition, from the viewpoint of improving foamability.

The cleansing composition of the invention may also comprise a polyol, and as a result, the moisture retaining property of skin can be further improved.

The polyol is a polyhydric alcohol having two or more hydroxy groups in the molecule, and specific examples thereof include alkylene glycol such as ethylene glycol, propylene glycol, 1,3-butylene glycol, and 1,4-butylene glycol; polyalkylene glycol such as dipropylene glycol; sugar alcohols such as glucose, maltose, maltitose, sucrose, fructose, xylitol, sorbitol, maltotriose, and threitol; glycerin, polyglycerin, erythritol, alcohol obtained by degradation and reduction of starch, and the like.

One or more types of polyol may be used. When it is contained, it is preferably contained in an amount of from 0.1 to 40% by weight, more preferably from 1 to 20% by weight, and even more preferably from 3 to 10% by weight in the total composition.

The cleansing composition of the present invention may also comprise other components used in ordinary cleansing composition such as an oily component, an anti-bacterial agent, an anti-inflammatory agent, a preservative, a chelating agent, salts, a pearlescent agent, a scrubbing agent, a fragrance, a cooling agent, a pigment, an UV absorbing agent, an antioxidant, plant extract, and the like.

The cleansing composition of the present invention may be produced by adding each component in order in water and dissolving them by fully stirring at 20 to 70° C. When a powder polymer is mixed, it is preferable that the polymer be first dispersed in water and then each component be mixed with each other.

The cleansing composition of the present invention preferably has pH of from 5 to 10, and more preferably pH of from 5.7 to 9.1 at 30° C. In the present invention, pH is measured after diluted 20 times by weight with water.

The cleansing composition of the present invention may be applied to a skin cleansing agent such as hand soap, hand wash, facial wash, cleansing foam, and body cleansing agent such as body soap, and also a hair cleansing agent such as shampoo. It is also preferred as a skin cleansing agent for body.

The method for cleansing skin by using the cleansing composition of the present invention is as follows. Specifically, the cleansing composition of the present invention is applied in an appropriate amount to a body, that is, a body skin part such as face, hand or feet, and torso, allowed to generate foams for cleansing, and rinsed off using hot water by shower, or the like. It is also possible that a suitable amount is added onto a cleansing aid tool such as towel, sponge, and brush and allowed to generate foams for cleansing.

With regard to the embodiments described above, the present invention also discloses the following composition, method, and use.

<1> A cleansing composition comprising the following components (A), (B), (C), and (D):

(A) from 1 to 20% by weight of a polyoxyethylene alkyl ether sulfate;

(B) from 0.02 to 5% by weight of a cation group-containing polymer having a cationic charge density of from 4.5 to 7 meq/g;

(C) from 0.02 to 10% by weight of cationized hydroxypropyl cellulose represented by the following formula (1);

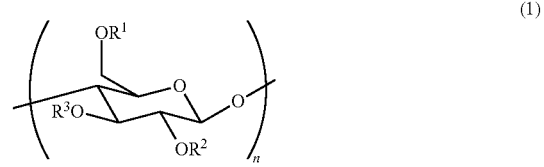

wherein $R^1$, $R^2$ and $R^3$ each independently represent a substituent group having a cationized ethylene oxy group and a propyleneoxy group represented by the formula (2) or (3), n represents a number of from 20 to 5000 which is a number representing the average polymerization degree of anhydroglucose, and the substitution degree of the cationized ethyleneoxy group is from 0.01 to 3 and the substitution degree of the propyleneoxy group is from 0.01 to 5,

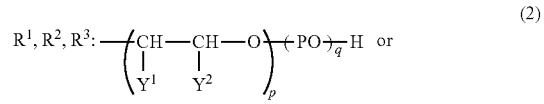

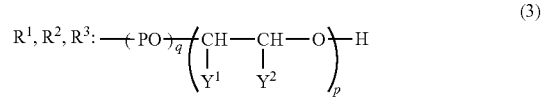

wherein one of $Y^1$ and $Y^2$ represents a hydrogen atom and the other represents a cationic group represented by the following formula (4), PO represents a propyleneoxy group, p represents the number of the cationized ethyleneoxy group ($—CH(Y^1)—CH(Y^2)—O—$) contained in the formula (2), q represents the number of the propyleneoxy group (—PO—), each representing 0 or a positive number, in which, when none of p and q is 0, the cationized ethyleneoxy group and the propyleneoxy group may be added in any order, and when at least one selected from p and q is 2 or higher, it may be any one of a block bond and a random bond,

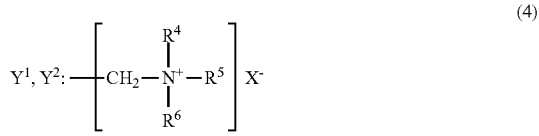

(4)

wherein R⁴, R⁵ and R⁶ each independently represent a linear or branched alkyl group having from 1 to 3 carbon atoms, and X⁻ represents an anionic group, and (D) water.

<2> The cleansing composition described in above <1>, further comprising (E) an inorganic salt or an organic acid salt having 6 or less carbon atoms.

<3> The cleansing composition described in above <1> or <2>, further comprising (F) a non-ionic polymer.

<4> The cleansing composition described in any one of above <1> to <3>, further comprising (G) at least one non-ionic surfactant selected from the group consisting of alkyl polyglycoside-based non-ionic surfactant and polyoxyethylene alkyl ether-based non-ionic surfactant.

<5> The cleansing composition described in any one of above <1> to <4>, in which the weight ratio between the components (B) and (C), that is, (C)/(B), is 0.1 or more, preferably 0.4 or more, and more preferably 0.6 or more, but 10 or less, preferably 4 or less, and more preferably 2 or less.

<6> The cleansing composition described in any one of above <2> to <5>, in which the weight ratio between the components (A), (B), (C), and (E), that is, (E)/((A)+(B)+(C)), is from 0.04 to 0.3 and preferably from 0.08 to 0.27.

<7> The cleansing composition described in any one of above <1> to <6>, in which the polyoxyethlyene alkyl ether sulfate as the component (A) has an average addition mole number of the polyoxyethylene of from 0.5 to 5, preferably from 0.9 to 4, and more preferably from 1 to 3, and has the alkyl group of from 12 to 14 carbon atoms.

<8> The cleansing composition described in any one of above <1> to <7>, in which the component (B) is one or two or more types selected from the group consisting of homopolymer of dimethyl diallylammonium chloride, copolymer of dimethyl diallylammonium chloride and acrylic acid, copolymer of dimethyl diallylammonium chloride and acrylic acid, and polymethacryloyloxyethyl trimethylammonium chloride.

<9> The cleansing composition described in any one of above <1> to <8>, in which cationic charge density of the component (B) is 4.5 meq/g or more, preferably from 4.5 to 7 meq/g, more preferably from 5 to 7 meq/g, and even more preferably from 5.5 to 6.5 meq/g.

<10> The cleansing composition described in any one of above <1> to <9>, in which, in the component (C), the average polymerization degree n in the formula (1) is 20 or higher, preferably 100 or higher, and more preferably 400 or higher, but 5000 or lower, preferably 2000 or lower, and more preferably 1300 or lower, the substitution degree of the cationized ethyleneoxy group is 0.01 or higher, preferably 0.1 or higher, and more preferably 0.18 or higher but 3 or lower, preferably 2.4 or lower, and more preferably 1 or lower, and the substitution degree of the propyleneoxy group is 0.01 or higher, preferably 0.2 or higher, and more preferably 1.1 or higher but 5 or less, preferably 3 or less, and more preferably 2.9 or less.

<11> The cleansing composition described in any one of above <2> to <10>, in which the component (E) may be salts between alkali metals or alkali earth metals and halogens, sulfuric acid, sulfurous acid, phosphoric acid and the like, specifically, one or two or more types of inorganic salts selected from the group consisting of sodium chloride, potassium chloride, sodium bromide, magnesium chloride, sodium sulfate, potassium sulfate, sodium dihydrogen phosphate, and disodium hydrogen phosphate, and preferably sodium chloride.

<12> The cleansing composition described in any one of above <2> to <10>, in which the component (E) is one or two or more types of salts with organic acid selected from the group consisting of acetic acid, sodium malate, sodium lactate, sodium citrate, and sodium succinate.

<13> The cleansing composition described in any one of above <3> to <12>, in which the component (F) is one or two or more types selected from the group consisting of hydroxyethyl cellulose, hydroxypropylmethyl cellulose, hydroxypropyl guar gum, polyvinyl pyrrolidone, and polyethylene glycol, and has a weight average molecular weight of preferably from 40,000 to 3,000,000, more preferably from 300,000 to 2,750,000, and even more preferably from 2,000,000 to 2,500,000.

<14> The cleansing composition described in any one of above <4> to <13>, in which, in the component (G), the alkyl polyglycoside-based non-ionic surfactant is one or two or more types selected from the group consisting of alkyl (C10-16) polyglucoside and alkyl (C9-11) glucoside and the polyoxyethylene alkyl ether-based surfactant is one or two or more types selected from the group consisting of polyoxyethylene (21) lauryl ether (HLB 14), polyoxyethylene (20) 2-hexyldecyl ether (HLB 14), polyoxyethylene (20) octyl dodecyl ether (HLB 13), and polyoxyethylene (16) lauryl ether (HLB 15.8), and preferably polyoxyethylene (16) lauryl ether.

<15> The cleansing composition described in any one of above <1> to <14>, in which the component (A) is, as a salt in the total composition, contained at 1% by weight or more, and preferably 3% by weight or more, but 20% by weight or less, and preferably 12% by weight or less.

<16> The cleansing composition described in any one of above <1> to <15>, in which the component (B) is contained at 0.02% by weight or more, preferably 0.1% by weight or more, and more preferably 0.2% by weight or more but 5% by weight or less, preferably 1.5% by weight or less, and more preferably 0.8% by weight or less in the total composition.

<17> The cleansing composition described in any one of above <1> to <16>, in which the component (C) is contained at 0.02% by weight or more, preferably 0.1% by weight or more, and more preferably 0.3% by weight or more but 10% by weight or less, and preferably 1.5% by weight or less in the total composition.

<18> The cleansing composition described in any one of above <2> to <17>, in which the component (E) is contained at 0.1% by weight or more, and preferably 0.5% by weight or more but 6% by weight or less, and preferably 3% by weight or less in the total composition.

<19> The cleansing composition described in any one of above <3> to <18>, in which the component (F) is contained at 0.01% by weight or more, and preferably 0.02% by weight or more but 0.8% by weight or less, and preferably 0.4% by weight or less in the total composition.

<20> The cleansing composition described in any one of above <4> to <19>, in which the component (G) is contained at 0.05% by weight or more, preferably 0.2% by weight or more, and more preferably 0.5% by weight or more but 10% by weight or less, preferably 6% by weight or less, and more preferably 4% by weight or less in the total composition.

<21> The cleansing composition described in any one of above <1> to <20>, which is a skin cleansing agent.

<22> A method for cleansing skin, comprising applying the cleansing composition described in any one of above <1> to <21> on a body skin part for cleansing followed by rinsing.

<23> Use of the cleansing composition described in any one of above <1> to <20> for production of a skin cleansing agent.

EXAMPLES

In the following examples, methods for measuring various physical properties are as follows.

(1) Measurement of Moisture Content in Pulp and Powder Cellulose:

Moisture content in pulp and powder cellulose was measured by using an infrared moisture tester ("FD-610", manufactured by Kett Electric Laboratory). The time point at which the weight change ratio was 0.1% or less for 30 seconds at measurement temperature of 120° C. was taken as the terminal point of the measurement.

(2) Calculation of Crystallinity of Pulp and Powder Cellulose

By using "Rigaku RINT 2500VC X-RAY diffractometer" manufactured by Rigaku Corporation, calculation was made on the basis of the following equation (1) from the peak intensity of diffraction spectrum which has been measured according to the following conditions.

X ray source: Cu/Kα-radiation, tube voltage: 40 kV, tube current: 120 mA

Measurement range: 2θ=5 to 45°

Measurement sample: prepared by compressing a pellet with area 320 mm²×thickness 1 mm X ray scan speed: 10°/min If the obtained crystallinity has a negative value, it was all given with crystallinity of 0%.

$$\text{Crystallinity}(\%) = [(I22.6 - I18.5)/I22.6] \times 100 \quad (1)$$

in the equation, I22.6 indicates diffraction intensity of lattice plane (002 plane) (diffraction angle 2θ=22.6°) and I18.5 indicates diffraction intensity of an amorphous part (diffraction angle 2θ=18.5° in X ray diffraction.

(3) Calculation of the Substitution Degree of Cationized Hydroxypropyl Cellulose (C-HPC) (Hereinafter, Also Referred to as Cationized Hydroxypropyl Cellulose "C-HPC"):

After purifying C-HPC obtained from Preparation Example by using a dialysis membrane (molecular weight cut off: 1000), the aqueous solution was subjected to freeze-drying to give purified C-HPC. Chlorine content (%) in the obtained purified C-HPC was measured by elemental analysis and, by approximating that the number of cationic groups that are contained in C-HPC was the same as the number chloride ions as a counter ion, amount (a (mol/g)) of the cationized ethyleneoxy group (—CH(Y1)-CH(Y2)O—) contained in the unit weight of C-HPC was obtained on the basis of the following equation (2).

$$a(\text{Mol/g}) = \text{Chloride content obtained by elemental analysis}(\%)/(35.5 \times 100) \quad (2)$$

Except that the subject for analysis was purified C-HPC instead of hydroxypropyl cellulose, content (%) of hydroxypropoxy group was measured according to the "Method for analysis of hydroxypropyl cellulose" described in Japanese Pharmacopoeia. Based on the following equation (3), content of hydroxypropoxy group (b mol/g) was obtained [formula amount ($OC_3H_6OH$=75.09)].

$$b(\text{Mol/g}) = \text{Content of hydroxypropoxy group obtained by gas chromatography analysis}(\%)/(75.09 \times 100)$$

From the obtained values a and b and also the following equations (4) and (5), substitution degree (k) of cationized ethyleneoxy group and substitution degree (m) of propyleneoxy group were calculated.

$$a = k/(162 + k \times K + m \times 58) \quad (4)$$

$$b = m/(162 + k \times K + m \times 58) \quad (5)$$

[in the formula, k and K represent the substitution degree and the formula value, respectively, of a cationized ethyleneoxy group and m represents the substitution degree of a propyleneoxy group].

(4) Calculation of Water Soluble Fractions:

Sample (0.50 g) was weighed in a 50 mL screw tube, 49.5 g of ion exchange water was added thereto, and dissolved by stirring for 12 hours with a magnetic stirrer. The solution (50 mL) was transferred to a centrifuge tube and centrifuged for 20 min at 3000 rpm (2000×g). The supernatant (5 mL) was dried under reduced pressure (105° C., 3 hours) to give a solid matter, and the water soluble fraction was calculated according to the following equation.

Water soluble fraction(%)=(Solid matter weight (g) in 5 mL supernatant×10/Sample weight)×100

(5) Measurement of Average Polymerization Degree (Copper Ammonia Method):

(5-1) Measurement of Viscosity Average Polymerization Degree of Pulp and Powder Cellulose;

(i) Preparation of Solution for Measurement; To a measuring flask (100 mL), copper (I) chloride (0.5 g) and 25% ammonia water (from 20 to 30 mL) were added. After complete dissolution, copper (II) hydroxide (1.0 g) and 25% ammonia water were added until it was right below the marked line. The resultant was stirred for from 30 to 40 min for complete dissolution. After that, precisely weighed cellulose was added and the ammonia water was filled up to the marked line. It was sealed to protect against air and stirred for 12 hours with a magnetic stirrer for dissolution. As a result, a solution for measurement was prepared. The addition amount of cellulose was changed in the range of from 20 to 500 mg to prepare a solution for measurement with different concentration.

(ii) Measurement of Viscosity Average Polymerization Degree;

The solution for measurement obtained from above (i) (that is, copper ammonia solution) was applied to an Ubbelohde viscometer. After keeping in a thermostat bath (20±0.1° C.) for 1 hour, the liquid flow rate was measured. From the flow time (t (sec)) of copper ammonia solution with various cellulose concentrations (d/gL) and flow time (t0 (sec)) of aqueous copper ammonia solution not including cellulose, the reduced viscosity (ηsp/c) at each concentration was calculated according to the following equation.

$$(\eta sp/c) = \{(t-t0)/t0\}/c$$

(c: cellulose concentration (g/dL))

Further, by extrapolating the reduced viscosity to c=0, intrinsic viscosity [η] (dL/g) was obtained and the viscosity average polymerization degree (DP) was obtained according to the following formula.

$$DP = 2000 \times [\eta]$$

(5-2) Measurement of Viscosity Average Polymerization Degree of C-HPC;

(iii) Preparation of Solution for Measurement;

Except that precisely weighed C-HPC was used instead of precisely weighed cellulose, a solution for measurement was prepared in the same manner as the preparation of a solution for measurement described in the above (i).

(iv) Measurement of Viscosity Average Polymerization Degree;

Except that cellulose equivalent concentration (g/dL) was employed as concentration of a solution for measurement, the measurement was performed in the same manner as the measurement of viscosity average polymerization degree described in above (ii).

As described herein, the cellulose equivalent concentration (ccell) indicates the weight (g) of the cellulose skeleton portion contained in 1 dL of the solution for measurement, and it is defined by the following equation (6).

$$ccell = u \times 162/(162 + k \times K + m \times 58) \quad (6)$$

[in the equation, u indicates the weight (g) of C-HPC which has been weighed and used for preparation of a solution for measurement, and k, K, and m each are the same as defined in the equation (4) and the equation (5)].

[Substitution Degree of Propyleneoxy Group (—PO—)]

Except that the subject for analysis was C-HPC obtained after purification using the dialysis membrane and freeze-drying instead of hydroxypropyl cellulose, the substitution degree of propyleneoxy group was measured according to the method for analysis of hydroxypropyl cellulose described in Japanese Pharmacopoeia.

Preparation Example 1

Preparation of C-HPC (1)

(1) Chipping Step:

Sheet-shape wood pulp (manufactured by Tembec, average polymerization degree of 1770, crystallinity of 74%, and moisture content of 8.5%) was prepared to be a chip-shape product after treatment using a sheet pelletizer ("SGG-220", manufactured by HORAI Co, Ltd.).

(2) Step of Adding Cationizing Agent and Lowering Crystallinity with an Aid of Mechanical Force:

The obtained chip-shape pulp (2.1 kg) and glycidyl trimethyl ammonium chloride (hereinafter, also referred to as "GMAC", manufactured by Sakamoto Yakuhin Kogyo Co., Ltd., moisture content of 20%, and purity of 90% or higher) (1.2 kg) (0.5 moles per mol of AGU) were mixed with each other in a bag and then supplied to a batch type vibration mill ("FV-20" manufactured by CHUO KAKOHKI Co., Ltd.: total vessel volume –68.9 L, 114 rods made of SUS304, in which each rod has φ of 30 mm, length of 590 mm, and round cross section, and filling ratio of 70%). By performing a treatment for lowering crystallinity for 12 min at frequency number of 20 Hz, total amplitude of 8 mm, and temperature of 30° C. or lower, a powder mixture of cellulose and GMAC (moisture content of 22.3% to cellulose, viscosity average polymerization degree of 1350, and crystallinity of 68%) was obtained.

(3) Step of Adding Base Compound and Lowering Crystallinity with an Aid of Mechanical Force To the powder mixture obtained from the step (2), NaOH powder (0.284 kg, that is, 0.6 moles per mol of AGU) was added and subjected to a treatment for lowering crystallinity for 20 min using a batch type vibration mill at frequency number of 20 Hz, total amplitude of 8 mm, and temperature of 50° C. or lower to obtain a powder mixture of cationized cellulose (hereinafter, also referred to as "C-Cell"), GMAC, and NaOH. Further, polypropylene glycol (manufactured by Wako Pure Chemical Industries, Ltd., trade name; "polypropylene glycol diol type average molecular weight of 1000" (PPG1000); weight average molecular weight of 1000) 0.192 kg (10% by weight per raw cellulose used in the step a)) was added to a batch type vibration mill for a treatment of lowering crystallinity for 120 min at frequency number of 20 Hz, total amplitude of 8 mm, and temperature of 50° C. or lower to give powder mixture (3.7 kg) of C-Cell, GMAC, NaOH, and PPG1000.

(4) Hydroxypropylation Step and Neutralization Step:

Powder mixture (10.0 kg) prepared by repeating several times the step (2) and the step (3) was added to a Pro Share mixer (75 L). After increasing the internal temperature to 56° C., 2.8 kg of propylene oxide (1.5 moles per mol of AGU) was sequentially added dropwise so that the reaction was performed until the internal pressure decreases according to consumption of propylene oxide. To 12.6 kg of the reaction product, 8.0 kg of 24% aqueous solution of lactic acid was added by spraying to give 20.6 kg of neutralization product.

The obtained neutralization product (15.2 kg) was added to a 65 L high speed mixer and dried under reduced pressure at internal temperature of from 70 to 80° C. to obtain the dry product (10.0 kg). The resulting dry product was pulverized by a pin mill and used as a powder.

The product was purified using a dialysis membrane (molecular weight cut off: 1000), and the aqueous solution was subjected to freeze-drying to give purified C-HPC (1). As a result of the analysis of the purified product, the substitution degrees of the cationic group and the propyleneoxy group were found to be 0.22 and 1.13, respectively. Further, the viscosity average polymerization degree of the obtained C-HPC (1) was found to be 693.

Preparation Example 2

Preparation of C-HPC (2)

(1) Chipping Step:

Sheet-shape wood pulp (Biofloc HV+ manufactured by Tembec, average polymerization degree of 1481, crystallinity of 74%, and moisture content of 4.6%) was prepared to be a chip-shape product (width and length; 3 to 5 mm) after treatment using a sheet pelletizer ("SGG-220", manufactured by HORAI Co, Ltd.).

(2) Step of Producing Alkali Cellulose

The chip-shape pulp (100 g) obtained from the above step (1) and 23.6 g of 0.7 mm particulate NaOH (equivalent to 1.0 mole per mol of AGU) were supplied to a batch type vibration mill ("MB-1" manufactured by CHUO KAKOHKI Co., Ltd.: total vessel volume of 3.5 L, 13 rods made of SUS304, in which each rod has φ of 30 mm, length of 218 mm, and round cross section, and filling ratio of 57%). After performing pulverizing treatment for 15 min (frequency number of 20 Hz, amplitude of 8 mm, and temperature of from 30 to 70° C.), the resulting mixture product of cellulose and NaOH was transferred to a mortar and 50 g of water was added thereto by spraying. It was then mixed for 5 min at 20° C. using a pestle and mortar to give alkali cellulose (average polymerization degree: 1175, crystallinity: 28%).

(3) Hydroxypropylation Step

The alkali cellulose obtained from the step (2) was added to a sealed reactor (manufactured by Nitto Koatsu, 1.5 L autoclave) and the inside of the reaction vessel was replaced with nitrogen. Subsequently, propylene oxide was sequentially added while stirring at constant inside vessel pressure of 0.05 MPa after increasing temperature to 50° C. followed by the reaction for 7 hours. The total addition amount of propylene oxide was 102 g (equivalent to 3.0 moles per mol of AGU).

(4) Cationizing Step:

The reaction mixture (30.0 g) obtained from the above step (3) was transferred to a mortar and 9.30 g (equivalent to 0.50 moles per mol of AGU) of 65% aqueous solution of 3-chloro-2-hydroxypropyltrimethyl ammonium chloride (manufactured by Yokkaichi Chemical Co., Ltd.) was added, followed by stirring for 5 min. After transfer to a 150 mL glass bottle, the reaction was allowed to occur for 7 hours at 50° C. to give crude C-HPC.

The crude C-HPC powder (5.0 g) was collected and neutralized with lactic acid. For the purpose of obtaining the substitution degrees of the propyleneoxy group and the cationized ethyleneoxy group, the neutralization product was purified by using a dialysis membrane (molecular weight cut off: 1000) and the aqueous solution was subjected to freeze-drying to give purified C-HPC (2).

As a result of the analysis of the purified product, the substitution degrees of the cationic group and the propyleneoxy group were found to be 0.18 and 2.0, respectively. Further, the viscosity average polymerization degree of the obtained C-HPC (2) was found to be 693.

Preparation Example 3

Preparation of C-HPC (3)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was prepared to be a chip-shape product (width and length; from 3 to 5 mm) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Step of Obtaining Alkali Cellulose (Step 1)

The obtained dry chip-shape pulp (920 g) was supplied to a vibration rod mill ("FV-10" manufactured by CHUO KAKOHKI Co., Ltd.: total vessel volume of 35 L, 63 rods are used in which each rod has diameter of 30 mm). After performing pulverizing treatment for 10 min (20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (II).

(Step 2)

Powdery pulp (460 g) obtained from above (step 1) as cellulose-containing raw material (II) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mole per mol of AGU of raw material (II) cellulose, and 33% of water per raw material (II) cellulose)) was added for 1.5 min by spraying. After the spraying, the internal temperature was increased to 50° C. and aged while stirring for 3 hours to obtain an alkali cellulose mixture.

(3) Hydroxypropylation Step:

The alkali cellulose mixture (720.5 g) obtained from above (2) was added to a Redige mixer and the temperature was increased to 50° C. while being stirred with main wing at 50 rpm and chopper wing at 400 rpm. After that, propylene oxide (571.4 g, equivalent to 3.5 moles per mol of AGU of the alkali cellulose) was added dropwise thereto for 3.5 hours. Once the dropwise addition was completed, it was aged for 2 hours at 50° C.

(4) Cationizing Step and Neutralization Step:

The reaction mixture (272.0 g) obtained from the hydroxypropylation was added to a mixer ("High Speed Mixer" with 2 L volume, manufactured by Fukae Pautec, Co., Ltd.). After increasing the internal temperature to 50° C., 65% aqueous solution of 3-chloro-2-hydroxypropyltrimethyl ammonium chloride (manufactured by Yokkaichi Chemical Co., Ltd.) (82.8 g, equivalent to 0.5 moles per mol of AGU which constitutes the cellulose skeleton of the compound containing cellulose skeleton in the reaction mixture that has been obtained by hydroxypropylation) was added for 1.5 min by spraying while being stirred with main wing at 337 rpm and chopper wing at 1800 rpm. After spraying, aging while stirring was performed for 2 hours to give crude C-HPC. Subsequently, 29% aqueous solution of lactic acid was sprayed for 1.5 min for neutralization of the crude C-HPC.

The crude C-HPC powder (5.0 g) was collected. For the purpose of obtaining the substitution degrees of the propyleneoxy group and the cationized ethyleneoxy group, the neutralization product was purified by using a dialysis membrane (molecular weight cut off: 1000) and the aqueous solution was subjected to freeze-drying to give purified C-HPC (3).

As a result of the analysis of the purified product, the substitution degrees of the cationic group and the propyleneoxy group were found to be 0.11 and 2.0, respectively. Further, the viscosity average polymerization degree of the obtained C-HPC (3) was found to be 743.

Preparation Example 4

Preparation of C-HPC (4)

(1) Chipping Step:

As cellulose, sheet-shape wood pulp (manufactured by Tembec, viscosity average polymerization degree of 1770, crystallinity of 74%, and moisture content of 7.6%) was prepared to be a chip-shape product after treatment using a sheet pelletizer ("SGG-220", manufactured by HORAI Co, Ltd.).

(2) Step of Adding Cationizing Agent and Lowering Crystallinity with an Aid of Mechanical Force:

The obtained chip-shape pulp (108 g) and glycidyl trimethyl ammonium chloride (hereinafter, also referred to as "GMAC", manufactured by Sakamoto Yakuhin Kogyo Co., Ltd., moisture content of 20%, and purity of 90% or higher) (23.4 g) (0.2 moles per unit mol of the anhydroglucose in cellulose (hereinafter, also referred to as "AGU")) were mixed with each other using a pestle and mortar and then supplied to a batch type vibration mill ("MB-1" manufactured by CHUO KAKOHKI Co., Ltd.: total vessel volume of 3.5 L, 13 rods made of SUS304, in which each rod has φ of 30 mm, length of 218 mm, and round cross section, and filling ratio of 57%). By performing a treatment for lowering crystallinity for 12 min at frequency number of 20 Hz, total amplitude of 8 mm, and temperature of 30° C. or lower, a powder mixture (131 g) of cellulose and GMAC (moisture content of 12.3% to cellulose, viscosity average polymerization degree of 1350, and crystallinity of 68%) was obtained.

(3) Step of Adding Base Compound and Lowering Crystallinity with an Aid of Mechanical Force:

The powdery pulp (131 g) obtained from above (2) was mixed with 24.7% aqueous sodium hydroxide solution (20 g, 0.2 moles per mol of AGU) using a pestle and mortar, and then supplied to a batch type vibration mill ("MB-1" manufactured by CHUO KAKOHKI Co., Ltd.: total vessel volume of 3.5 L, 117 rods made of SUS304, in which each rod has φ of 10 mm, length of 218 mm, and round cross section, and filling ratio of 57%). By performing a treatment for lowering crystallinity for 60 min at frequency number of 20 Hz, total amplitude of 8 mm, and temperature of 30° C. or lower, a powder mixture (151 g) of C-Cell, GMAC, and sodium hydroxide (moisture content of 27.4% to cellulose, viscosity average polymerization degree of 1330, and crystallinity of 45%) was obtained. The powdery mixture (5 g) was collected, neutralized with acetic acid, and washed three times with 85% aqueous solution of isopropyl alcohol (100 mL) for desalting and purification. Subsequently, according to drying under reduced pressure, purified cationized cellulose (4 g, viscosity average polymerization degree: 1330, crystallinity: 45%) was obtained.

As a result of the elemental analysis, the substitution degree of cationic group was calculated to be 0.1. Further, the water soluble fraction was 31%.

(4) Hydroxypropylation Step and Neutralization Step:

The obtained cationized cellulose (100 g, non-neutralized and non-purified product) was injected to a 1 L kneader equipped with a reflux condenser (PNV-1 type, manufactured by IRIE SHOKAI Co., Ltd.). The jacket part of the kneader was heated to 70° C. by hot water and propylene oxide (141.9 g, 6 moles per mole of AGU, manufactured by Kanto Chemical Co., Inc., special grade reagent) was added dropwise thereto under nitrogen atmosphere and the reaction was performed for 40 hours until the reflux stops according to consumption of propylene oxide.

The product was collected from the kneader to give crude C-HPC powder with pale brown color (240 g). 10.0 g of the reaction product was collected and neutralized with acetic acid to give a pale brown solid. The product was purified by using a dialysis membrane (cut off molecular weight: 1000) and the aqueous solution was subjected to freeze-drying to give purified C-HPC (4).

From the content of the propyleneoxy group [molecular weight (C3H6O)=58.08] obtained by the hydroxypropyl cellulose analysis, the substitution degree of the propyleneoxy group was found to be 2.9. Further, the water soluble fraction of the obtained C-HPC (4) was found to be 71% and the viscosity average polymerization degree was found to be 1,300.

Preparation Example 5

Preparation of C-HPC (5)

(1) Preparation of Dry Powder Cellulose:

Powder cellulose (manufactured by NIPPON PAPER Chemicals Co., Ltd., cellulose powder KC FLOCK W-400G, average polymerization degree: 191, crystallinity: 77%, and moisture content: 7.0%) was dried for 12 hours at 50° C. under reduced pressure to obtain dry powder cellulose (moisture content: 1.0%).

(2) Cationizing Step (1):

The obtained powder cellulose (100 g) was mixed with GMAC (60.8 g) using a pestle and mortar and added to the vibration mill described in the Preparation Example 1. After pulverization treatment for 12 min (frequency number of 20 Hz, total amplitude of 8 mm, and temperature of from 10 to 40° C.), powdery mixture of cellulose and GMAC was obtained.

Further, 48% aqueous solution of sodium hydroxide (29.8 g) was added to the vibration mill, and a pulverization treatment under the same pulverization condition using the vibration mill was performed for 60 min to give cationized cellulose.

(3) Hydroxypropylation Step:

A kneader to which the cationized cellulose (190 g) obtained from the above step was added was heated to 70° C., and then propylene oxide (18.0 g) was added dropwise while stirring, and the reaction was allowed to occur for 6 hours until the reflux stops according to consumption of propylene oxide.

(4) Cationizing Step (2):

The mixture after the reaction was transferred from the kneader to a mortar, GMAC (87.5 g, equivalent to 0.8 moles per mol of AGU) was added, and stirred for 10 min at room temperature. After that, it was brought back to the kneader, and the reaction was performed while stirring for 5 hours at 50° C. to give crude C-HPC powder with pale brown color (295 g).

To the obtained crude C-HPC powder, GMAC (87.5 g) was added again and the procedure up to the reaction at 50° C. was similarly carried out. The above procedures were repeated seven times in total (total amount of the added propylene oxide was 612.5 g; equivalent to 5.3 moles per mol of AGU). The reaction product (10.0 g) was collected and neutralized with lactic acid to obtain pale brown solid. For the purpose of obtaining the substitution degrees of the propyleneoxy group and cationized ethyleneoxy group, the product was purified by using a dialysis membrane (molecular weight cut off: 1000) and the aqueous solution was subjected to freeze-drying to give purified C-HPC (5).

As a result of the analysis of the purified product, the substitution degrees of the cationized ethyleneoxy group and the propyleneoxy group in the obtained purified C-HPC (5) were found to be 2.36 and 0.2, respectively. Further, the average polymerization degree was found to be 432.

Preparation Example 6

Preparation of C-HPC (6)

(1) Chipping Step:

Sheet-shape wood pulp (Biofloc HV+ manufactured by Tembec, average polymerization degree of 1604, α-cellulose content of 93.0%, crystallinity of 74%, and moisture content of 7.0%) was prepared to be a chip-shape product (width and length; from 3 to 5 mm) after treatment using a sheet pelletizer ("SGG-220", manufactured by HORAI Co, Ltd.).

The obtained chip-shape pulp was added to a vacuum dryer (product name: VO-402, manufactured by Advantec Toyo Kaisha, Ltd.) and dried for 2 hours at 105° C., 20 kPa under nitrogen stream to give dry chip-shape pulp (average polymerization degree: 1604, α-cellulose content: 99.2%, crystallinity: 74%, and moisture content: 0.8%).

(2) Step of Producing Alkali Cellulose (Step 1)

The obtained dry chip-shape pulp (920 g) was supplied to a vibration rod mill ("FV-10" manufactured by CHUO KAKOHKI Co., Ltd.: total vessel volume of 35 L, 63 rods are used in which each rod has diameter of 30 mm). After performing pulverizing treatment for 10 min (frequency number of 20 Hz, amplitude of 8 mm, and temperature of from 10 to 40° C.), powdery pulp with lowered crystallinity (920 g, average polymerization degree: 1198, crystallinity: 14%, moisture content: 1.0%) was obtained as cellulose-containing raw material (II).

21

(Step 2)

Powdery pulp (460 g) obtained from above (step 1) as cellulose-containing raw material (II) was supplied to a mixer ("Redige mixer" with volume of 5 L, manufactured by MATSUBO Corporation), and while being stirred with main wing at 250 rpm and chopper wing at 2500 rpm, 42.5% aqueous solution of sodium hydroxide (266.8 g (equivalent to 1.0 mole per mol of AGU of raw material (II) cellulose, and 33% of water per raw material (II) cellulose)) was added for 1.5 min by spraying. After the spraying, the internal temperature was increased to 50° C. and aged while stirring for 3 hours to obtain an alkali cellulose mixture.

(3) Hydroxypropylation Step:

The alkali cellulose mixture (720.5 g) obtained from above (2) was added to a Redige mixer and the temperature was increased to 50° C. while being stirred with main wing at 50 rpm and chopper wing at 400 rpm. After that, propylene oxide (571.4 g, equivalent to 3.5 moles per mol of AGU of the alkali cellulose) was added dropwise thereto for 3.5 hours. Once the dropwise addition was completed, it was aged for 2 hours at 50° C.

(4) Cationizing Step and Neutralization Step:

The reaction mixture obtained from the hydroxypropylation step was aged by keeping it for 6 months in a refrigerator (5° C.) to have slow degradation of sugar chain. The reaction mixture after low temperature aging (5.0 g) and 65% aqueous solution of 3-chloro-2-hydroxypropyltrimethyl ammonium chloride (manufactured by Yokkaichi Chemical Co., Ltd.) (1.38 g, equivalent to 0.45 moles per mol of AGU which constitutes the cellulose skeleton of the compound containing cellulose skeleton in the reaction mixture that has been obtained by hydroxypropylation) were mixed with each other using a pestle and mortar, and aged by keeping it for 5 hours in a sealed reactor (50° C.) to prepare crude C-HPC. Subsequently, 29% aqueous solution of lactic acid was used for neutralization of the crude C-HPC.

The crude C-HPC powder (2.0 g) was collected. For the purpose of obtaining the substitution degrees of the propyleneoxy group and cationized ethyleneoxy group, the neutralization product was purified by using a dialysis membrane (molecular weight cut off: 1000) and the aqueous solution was subjected to freeze-drying to give purified C-HPC (6).

As a result of the analysis of the purified product, the substitution degrees of the cationic group and the propyleneoxy group were found to be 0.20 and 2.1, respectively. Further, the viscosity average polymerization degree of the obtained C-HPC (6) was found to be 100.

TABLE 1

| | | Average polymerization degree | Substitution degree of cationized EO *1 | Substitution degree of PO *2 |
|---|---|---|---|---|
| Preparation Example 1 | C-HPC(1) | 693 | 0.22 | 1.13 |
| Preparation Example 2 | C-HPC(2) | 693 | 0.18 | 2.0 |
| Preparation Example 3 | C-HPC(3) | 743 | 0.11 | 2.0 |
| Preparation Example 4 | C-HPC(4) | 1300 | 0.10 | 2.9 |
| Preparation Example 5 | C-HPC(5) | 432 | 2.36 | 0.2 |
| Preparation Example 6 | C-HPC(6) | 100 | 0.20 | 2.1 |

*1: Substitution degree of cationized ethyleneoxy group (p)
*2: Substitution degree of propyleneoxy group (q)

22

Examples 1 to 12 and Comparative Examples 1 and 2

The cleansing composition having the composition listed in Table 2 was produced according to the following method. Quickness of lathering, foam quality, foam volume during cleansing, low slimy feel during rinsing, easy disappearance of slimy feel during rinsing, strength of stop feeling property after rinsing, and skin feel after drying were evaluated for the obtained cleansing composition. The results are also listed in Table 2.

(Preparation method)

After dispersing powdery C-HPC in water at 20° C., each component was mixed in order, fully stirred, and dissolved to give a cleansing composition.

(Evaluation Method)

(1) Quickness of Lathering:

Each cleansing composition (1 g) was collected by hands, diluted by five times approximately with tap water at 30° C. After briefly generating foams for 5 seconds with both hands, quickness of lathering was evaluated. The evaluation was made based on the following criteria, and expressed as an average value given by five professional panelists.

5; It was felt that the lathering (ability) was very fast.
4; It was felt that the lathering (ability) was fast.
3; It was felt that the lathering (ability) was moderate.
2; It was felt that the lathering (ability) was slightly slow.
1; It was felt that the lathering (ability) was slow.

(2) Foam Quality (Creaminess):

Each cleansing composition (1 g) was collected by hands, diluted by five times approximately with tap water at 30° C. After briefly generating foams for 20 seconds with both hands, foam quality (creaminess) was evaluated. The evaluation was made based on the following criteria, and expressed as an average value given by five professional panelists.

5; It was felt that foam quality was fine, very creamy, and thus the foam quality was found to be good.
4; It was felt that foam quality was creamy, and thus the foam quality was found to be good.
3; It was felt that foam quality was slightly creamy.
2; It was felt that foam quality was slightly light and rough.
1; It was felt that foam quality was light and rough.

(3) Foam Volume During Cleansing:

Each cleansing composition (1 g) was collected by one hand, diluted by five times approximately with tap water. After briefly generating foams for 20 seconds with both hands, foam volume was evaluated. The evaluation was made based on the following criteria, and expressed as an average value given by five professional panelists.

5; foam volume was felt to be very large.
4; foam volume was felt to be large.
3; foam volume was felt to be moderate.
2; foam volume was felt to be slightly small.
1; foam volume was felt to be small.

(4) Low Slimy Feel at the Start of Rinsing:

Each cleansing composition (1 g) was collected by one hand, and diluted by five times approximately with tap water at 30° C. After briefly generating foams for 20 seconds with both hands, the foams were collected in palm of one hand and used for cleansing the other arm (that is, from elbow to wrist). After cleansing, foams on the cleansed arm were washed off twice with tap water (12 mL) in the hand used for cleansing. At that time, strength of slimy feel was evaluated by five professional panelists. The evaluation was made based on the following criteria, and expressed as an average value given by five professional panelists.

5; there was almost no slimy feel.

4; there was weak slimy feel.

3; there was slimy feel.

2; there was somewhat strong slimy feel.

1; there was strong slimy feel.

(5) Easy Disappearance of Slimy Feel During Rinsing:

Each cleansing composition (1 g) was collected by one hand, and diluted by five times approximately with tap water at 30° C. After briefly generating foams for 20 seconds with both hands, the foams were collected in palm of one hand and used for cleansing the other arm (that is, from elbow to wrist). After cleansing, foams on the cleansed arm were washed off twice by spraying tap water (12 mL) in the hand used for cleansing. Again, tap water (12 mL) in the hand used for cleansing was sprayed once on the arm and the hand was rubbed against the arm. By having those steps as single rubbing process, the number of the rubbing until stop feeling was sensed was counted. The results were expressed as an average value given by five professional panelists.

(6) Strength of Stop Feeling Property Upon Completion of Rinsing:

Each cleansing composition (1 g) was collected by one hand, and diluted by five times approximately with tap water at 30° C. After briefly generating foams for 20 seconds with both hands, the foams were collected in palm of one hand and used for cleansing the other arm (that is, from elbow to wrist). After cleansing, foams on the cleansed arm were washed off twice by spraying tap water (12 mL) in the hand used for cleansing. Again, tap water (12 mL) in the hand used for cleansing was sprayed once on the arm and the hand was rubbed against the arm. By having those steps as single process, tap water was sprayed for continuous rinsing until stop feeling was sensed. Strength of stop feeling upon when stop feeling was sensed at the time of completing rinsing was evaluated. The evaluation was made based on the following criteria, and expressed as an average value given by ten professional panelists.

5; It was felt that the stop feeling was very strong at the time of finishing rinsing.

4; It was felt that the stop feeling was strong at the time of finishing rinsing.

3; Stop feeling was felt at the time of finishing rinsing.

2; Not much of stop feeling was felt at the time of finishing rinsing.

1; Stop feeling was not felt at the time of finishing rinsing.

(7) Skin Feel after Drying:

Ten professional panelists washed their whole bodies once a day with each cleansing composition. The same procedure was repeated consecutively for three days. Ten minutes after towel blotting, the number of people who replied that they felt strongly a skin feeling like being protected with a smooth film without stickiness was counted.

TABLE 2

| | Component (% by weight) | Example 1 | 2 | 3 | 4 | 5 | 6 | 7 | 8 |
|---|---|---|---|---|---|---|---|---|---|
| (A) | Sodium polyoxyethylene (1) lauryl ether sulfate *1 | 6.00 | 6.00 | 6.00 | 6.00 | 6.00 | 6.00 | 6.00 | 6.00 |
| (B) | homopolymer of dimethyl diaryl ammonium chloride *2 | 0.20 | 0.20 | 0.20 | 0.20 | 0.20 | 0.20 | 0.15 | 0.20 |
| (C) | C-HPC (1) (cationizing degree: 0.22, PO substitution degree: 1.13) | 0.40 | 0.40 | 0.40 | 0.40 | 0.40 | 0.40 | 1.50 | 0.60 |
| | C-HPC (2) (cationizing degree: 0.18, PO substitution degree: 2.0) | | | | | | | | |
| (D) | water | balance | balance | balance | balance | balance | balance | balance | balance |
| (E) | sodium chloride | | 1.50 | | | | | | |
| | sodium malate | | | 1.50 | 1.50 | 1.50 | 1.50 | 1.50 | 1.50 |
| (F) | polyethylene glycol *3 | | | | 0.02 | 0.02 | 0.02 | | |
| (G) | lauryl glucoside *4 | | | | | 3.00 | 3.00 | 3.00 | 3.00 |
| (H) | lauric acid amide propylbetaine *5 | | | | | | 3.00 | 3.00 | 3.00 |
| | dimethyl diallyl ammonium chloride • acrylamide (50:50) copolymer *6 | | | | | | | | |
| | hydroxyethyl cellulose hydroxypropyl trimethyl ammonium chloride ether *7 | | | | | | | | |
| | methyl polysiloxane *8 | | | | | | | | |
| | total | 100 | 100 | 100 | 100 | 100 | 100 | 100 | 100 |
| | (C)/(B) weight ratio | 2.00 | 2.00 | 2.00 | 2.00 | 2.00 | 2.00 | 10.00 | 3.00 |
| | (E)/((A) + (B) + (C)) | | 0.227 | 0.227 | 0.227 | 0.227 | 0.227 | 0.196 | 0.221 |
| | ((B) + (C))/(A) | 0.100 | 0.100 | 0.100 | 0.100 | 0.100 | 0.100 | 0.275 | 0.133 |
| | quickness of lathering | 4.2 | 4.2 | 4.2 | 4.2 | 4.2 | 4.4 | 4.4 | 4.4 |
| | foam quality (creaminess) | 4.4 | 4.4 | 4.4 | 4.6 | 4.6 | 4.6 | 4.6 | 4.6 |
| | foam volume during cleansing | 4.2 | 4.2 | 4.2 | 4.2 | 4.6 | 4.6 | 4.6 | 4.6 |
| | low slimy feel at the start of rinsing | 4.8 | 4.6 | 4.6 | 4.6 | 4.4 | 4.4 | 4.2 | 4.4 |
| | easy disappearance of slimy feel during rinsing (number) | 10.2 | 6.4 | 6.4 | 6.4 | 6.8 | 7 | 10 | 6.4 |
| | strength of stop feeling after finishing rinsing (average value obtained from 10 people) | 3.8 | 4.4 | 4.4 | 4.4 | 4.6 | 4.4 | 4 | 4.4 |
| | skin feel after drying; non-sticky feel like being protected by smooth film (number of people) | 9 | 9 | 9 | 9 | 9 | 9 | 7 | 8 |

TABLE 2-continued

|  | Component (% by weight) | Example 9 | Example 10 | Example 11 | Example 12 | Comparative Example 1 | Comparative Example 2 |
|---|---|---|---|---|---|---|---|
| (A) | Sodium polyoxyethylene (1) lauryl ether sulfate *1 | 6.00 | 6.00 | 6.00 | 6.00 | 6.00 | 6.00 |
| (B) | homopolymer of dimethyl diaryl ammonium chloride *2 | 0.50 | 0.80 | 1.50 | 0.20 | | |
| (C) | C-HPC (1) (cationizing degree: 0.22, PO substitution degree: 1.13) | 0.30 | 0.30 | 0.15 | | | |
|  | C-HPC (2) (cationizing degree: 0.18, PO substitution degree: 2.0) | | | | 0.40 | | |
| (D) | water | balance | balance | balance | balance | balance | balance |
| (E) | sodium chloride | | | | | | |
|  | sodium malate | 1.50 | 1.50 | 1.50 | 1.50 | | |
| (F) | polyethylene glycol *3 | | | | | | |
| (G) | lauryl glucoside *4 | 3.00 | 3.00 | 3.00 | 3.00 | | |
| (H) | lauric acid amide propylbetaine *5 | 3.00 | 3.00 | 3.00 | 3.00 | | |
|  | dimethyl diallyl ammonium chloride • acrylamide (50:50) copolymer *6 | | | | | | 0.20 |
|  | hydroxyethyl cellulose hydroxypropyl trimethyl ammonium chloride ether *7 | | | | | | 0.40 |
|  | methyl polysiloxane *8 | | | | | 1.00 | |
|  | total | 100 | 100 | 100 | 100 | 100 | 100 |
|  | (C)/(B) weight ratio | 0.60 | 0.38 | 0.10 | 2.00 | | |
|  | (E)/((A) + (B) + (C)) | 0.221 | 0.211 | 0.196 | 0.242 | | |
|  | ((B) + (C))/(A) | 0.133 | 0.183 | 0.275 | 0.100 | | |
|  | quickness of lathering | 4.4 | 4.4 | 4.4 | 4.4 | 2 | 3 |
|  | foam quality (creaminess) | 4.6 | 4.6 | 4.6 | 4.6 | 3 | 3.2 |
|  | foam volume during cleansing | 4.6 | 4.6 | 4.4 | 4.6 | 2 | 3 |
|  | low slimy feel at the start of rinsing | 4.4 | 4.4 | 4.2 | 4.8 | 1.2 | 2.8 |
|  | easy disappearance of slimy feel during rinsing (number) | 7 | 6.6 | 9.6 | 6.6 | 30.2 | 18 |
|  | strength of stop feeling after finishing rinsing (average value obtained from 10 people) | 4.4 | 4.6 | 4 | 4.9 | 1.6 | 3.2 |
|  | skin feel after drying; non-sticky feel like being protected by smooth film (number of people) | 9 | 8 | 7 | 9 | 6 | 2 |

*1: manufactured by Kao Corporation, effective component of EMAL 170J
*2: manufactured by Ondeo Nalco Company, effective component of MERQUAT 100 (cation charge density: 6.2 meq/g)
*3: manufactured by Meisei Chemical Works, Ltd., effective component of ALKOX E-100
*4: manufactured by Kao Corporation, effective component of AG-124
*5: manufactured by Kao Corporation, effective component of AMPHITOL 20AB
*6: manufactured by Ondeo Nalco Company, effective component of MERQUAT 550 (cation charge density: 3.1 meq/g)
*7: manufactured by Dow Chemical Company, effective component of UCARE POLYMER LR400 (cation charge density 1 meq/g)
*8: manufactured by Shin-Etsu Chemical Co., Ltd., effective component of silicone KF-96L-10CS

Examples 13 to 21

The cleansing composition having the composition listed in Table 3 was produced in the same manner as Examples 1 to 12.

All the obtained cleansing compositions were found to have a fast lathering ability, foam quality with fine texture, high creaminess, large foam volume during cleansing, no slimy feel during rinsing, and after drying, smooth feel with no stickiness.

TABLE 3

|  | component (% by weight) | 13 | 14 | 15 | 16 | 17 | 18 | 19 | 20 | 21 |
|---|---|---|---|---|---|---|---|---|---|---|
| (A) | sodium polyoxyethylene (1) lauryl ether sulfate *1 | | 2.00 | 12.00 | 10.00 | 6.00 | | 9.50 | 6.00 | 10.00 |
|  | sodium polyoxyethylene (2) lauryl ether sulfate *2 | 1.00 | 1.00 | | 10.00 | 2.00 | | | 2.00 | 2.00 |
|  | ammonium polyoxyethylene (1) alkyl ether sulfate *3 | | | | | | 10.00 | | | |
| (B) | homopolymer of dimethyl | | | 0.20 | 3.00 | | | 0.10 | | 0.40 |

TABLE 3-continued

| | component (% by weight) | 13 | 14 | 15 | 16 | 17 | 18 | 19 | 20 | 21 |
|---|---|---|---|---|---|---|---|---|---|---|
| | diallyl ammonium chloride *4 | | 0.10 | | 2.00 | 2.00 | 0.20 | | 2.00 | 0.40 |
| | dimethyl diallyl ammonium chloride • acrylic acid (97:3) copolymer *5 | | | | | | | | | |
| | dimethyl diallyl ammonium chloride • acrylic acid (80:20) copolymer *6 | 0.02 | | | | | 0.20 | 0.20 | | |
| (C) | C-HPC (1) (cationizing degree: 0.22, PO substitution degree: 1.13) | | | 0.30 | 0.20 | | | | 2.00 | 0.50 |
| | C-HPC (2) (cationizing degree: 0.18, PO substitution degree: 2.0) | 0.02 | 0.05 | 0.30 | 0.20 | 10.00 | 0.30 | | 2.00 | |
| | C-HPC (3) (cationizing degree: 0.11, PO substitution degree: 2.0) | | 0.05 | | 0.20 | | | | 2.00 | |
| | C-HPC (4) (cationizing degree: 0.1, PO substitution degree: 2.9) | | | | 0.20 | | 0.30 | | 2.00 | |
| | C-HPC (5) (cationizing degree: 2.36, PO substitution degree: 0.2) | | | 0.20 | | | | 0.20 | 2.00 | |
| | C-HPC (6) (cationizing degree: 0.2, PO substitution degree: 2.1) | | | | | | | | | 0.30 |
| (D) | water | balance | balance | balance | balance | balance | balance | balance | balance | balance |
| (E) | sodium chloride | 0.10 | 0.50 | | 3.00 | 6.00 | | 0.40 | 3.00 | |
| | sodium malate | | | 3.50 | | | 0.90 | | 3.00 | 3.00 |
| (F) | polyethylene glycol *7 | 0.005 | 0.01 | | 0.01 | 0.40 | 0.01 | 0.01 | | 0.20 |
| | hydroxypropyl guar gum *8 | | | 0.05 | | 0.20 | 0.02 | 0.20 | 0.10 | 0.20 |
| | hydroxypropylmethyl cellulose *9 | | | 0.35 | 0.30 | 0.20 | | 0.50 | 0.30 | |
| (G) | alkyl (C10-16) polyglucoside *10 | 0.20 | | | 2.00 | 2.00 | 2.00 | 5.00 | 2.00 | 2.00 |
| | alkyl (C9-11) glucoside *11 | | 0.05 | 0.50 | | 2.00 | | 5.00 | 2.00 | |
| | polyoxyethylene (16) lauryl ether *12 | | | | 1.00 | 2.00 | 2.00 | | 2.00 | 2.00 |
| (H) | lauric acid amide propylbetaine *13 | 2.00 | 0.10 | 1.00 | 0.20 | 3.00 | | | 3.00 | |
| | cocoamide propylbetaine *14 | | | 2.00 | 0.30 | | 0.20 | 5.00 | | 0.50 |
| | laurylhydroxy sulfobetaine *15 | 0.50 | | 2.00 | | 3.00 | 0.30 | 5.00 | 3.00 | |
| | sodium polyoxyethylene (2.6) lauryl ether carboxylate *16 | 0.05 | 0.50 | | 2.00 | | 3.00 | | | |
| | sodium polyoxyethylene (4.5) lauryl ether carboxylate *17 | 0.05 | 0.50 | | 1.00 | | 3.00 | | | |
| | potassium laurate | 3.00 | | | | 1.00 | | 7.00 | 1.00 | |
| | potassium myristate | 4.00 | | | | 2.00 | | 2.00 | 2.00 | |
| | potassium palmitate | 4.00 | | | | 2.00 | | 9.00 | 2.00 | |
| | potassium stearate | | | | | | | 1.00 | | |
| | sodium cocoylglutamate | | 3.00 | 3.00 | | 10.00 | | | 10.00 | |
| | propylene glycol | 1.00 | | 1.00 | 5.00 | | | 1.00 | | 4.00 |
| | dipropylene glycol | | 1.00 | | 1.00 | | 2.00 | | | |
| | glycerin | | 4.00 | | | 2.00 | | 1.00 | 2.00 | |
| | sorbitol | 5.00 | | 2.00 | | 3.00 | 2.00 | | 3.00 | |
| | pH adjuster | q.s. | q.s. | q.s. | q.s. | q.s. | q.s. | q.s. | q.s. | q.s. |
| | total | 100 | 100 | 100 | 100 | 100 | 100 | 100 | 100 | 100 |
| | (C)/(B) weight ratio | 1.0 | 1.0 | 4.0 | 0.2 | 5.0 | 1.5 | 0.7 | 5.0 | 0.6 |
| | (E)/((A) + (B) + (C)) | 0.10 | 0.16 | 0.27 | 0.12 | 0.30 | 0.08 | 0.04 | 0.30 | 0.23 |
| | ((B) + (C))/(A) | 0.04 | 0.07 | 0.08 | 0.29 | 1.50 | 0.10 | 0.05 | 1.50 | 0.11 |
| | pH (20 times dilution) | 8.8 | 6.9 | 7.0 | 5.9 | 9.0 | 5.7 | 9.1 | 9.0 | 6.5 |

*1: manufactured by Kao Corporation, effective component of EMAL 170J
*2: manufactured by Kao Corporation, effective component of EMAL 227
*3: manufactured by Kao Corporation, effective component of EMAL 125A
*4: manufactured by Ondeo Nalco Company, effective component of MERQUAT 100 (cation charge density 6.2 meq/g)
*5: manufactured by Ondeo Nalco Company, effective component of MERQUAT 295 (cation charge density 6.0 meq/g)
*6: manufactured by Ondeo Nalco Company, effective component of MERQUAT 280 (cation charge density 5.0 meq/g)
*7: manufactured by Meisei Chemical Works, Ltd., effective component of ALKOX E-100
*8: manufactured by Rhodia, effective component of JAGUAR HP-105
*9: manufactured by Shin-Etsu Chemical Co., Ltd., effective component of METOLOSE 60SH-10000
*10: manufactured by Kao Corporation, effective component of AG-124
*11: manufactured by Kao Corporation, effective component of AG-10LK
*12: manufactured by Kao Corporation, effective component of EMULGEN 116
*13: manufactured by Kao Corporation, effective component of AMPHITOL 20AB
*14: manufactured by Kao Corporation, effective component of AMPHITOL 55AB
*15: manufactured by Kao Corporation, effective component of AMPHITOL 20HD
*16: manufactured by Kao Corporation, effective component of AKYPO 26
*17: manufactured by Kao Corporation, effective component of KAOAKYPO RLM-45NV
*18: manufactured by Ajinomoto Co., Inc., effective component of AMILITE GCK-11

The invention claimed is:

1. A method for cleansing skin, comprising:
applying a composition to skin; and rinsing the composition off the skin,
wherein the cleansing composition comprises components (A), (B), (C), and (D):
(A) from 1 to 20% by weight of a polyoxyethylene alkyl ether sulfate;
(B) from 0.02 to 5% by weight of a cation group-containing polymer having a cationic charge density of from 4.5 to 7 meq/g;
(C) from 0.02 to 10% by weight of cationized hydroxypropyl cellulose; and
(D) water;
the cationized hydroxypropyl cellulose is of formula (1):

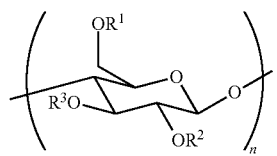

(1)

each of $R^1$, $R^2$, $R^3$ is independently a group having a cationized ethyleneoxy group and a propyleneoxy group of formula (2) or (3):

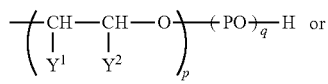

(2)

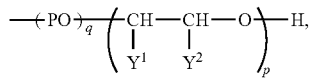

(3)

n, which is an average polymerization degree of anhydroglucose, is from 20 to 5000,
an average mole number of the cationized ethyleneoxy group present in a molecule of the cationized hydroxypropyl cellulose per mole of anhydroglucose units is from 0.01 to 3,
an average mole number of the propyleneoxy group present in a molecule of the cationized hydroxypropyl cellulose per mole of anhydroglucose units is from 0.01 to 5,
in each of formula (2) and formula (3), one of $Y^1$ and $Y^2$ is a hydrogen atom and the other is a cationic group of formula (4):

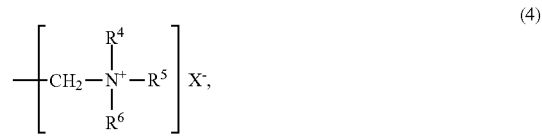

(4)

in each of formula (2) and formula (3), PO is a propyleneoxy group,
p, a number of the cationized ethyleneoxy group (—CH($Y^1$)—CH($Y^2$)—O—) in formula (2) or (3), is 0 or 1,
q, a number of the propyleneoxy group (—PO—) in formula (2) or (3), is from 0 to 4,
when neither p nor q is 0, cationized ethyleneoxy groups and propyleneoxy groups may be arranged in any order,
when p is 1 and q is 2 or higher, cationized ethyleneoxy groups and propyleneoxy groups may be arranged in blocks or randomly,
in formula (4), each of $R^4$, $R^5$, and $R^6$ is independently a linear or branched alkyl group having from 1 to 3 carbon atoms, and
$X^-$ is an anionic group.

2. The method according to claim 1, wherein the weight ratio between the components (B) and (C), (C)/(B), is from 0.1 to 10.

3. The method according to claim 1, wherein the composition further comprises (E) an inorganic salt or an organic acid salt having 6 or less carbon atoms.

4. The method according to claim 3, wherein the weight ratio between the components (A), (B), (C), and (E), (E)/((A)+(B)+(C)), is from 0.04 to 0.6.

5. The method according to claim 1, wherein the weight ratio between the components (A), (B), and (C), ((B)+(C))/(A), is from 0.04 to 0.3.

6. The method according to claim 1, wherein the composition further comprises (F) a non-ionic polymer.

7. The method according to claim 1, wherein the composition further comprises (G) at least one member selected from the group consisting of an alkyl polyglycoside-based non-ionic surfactant and a polyoxyethylene alkyl ether-based non-ionic surfactant.

* * * * *